(12) United States Patent
Erdman et al.

(10) Patent No.: US 6,548,732 B2
(45) Date of Patent: Apr. 15, 2003

(54) ABSORBENT ARTICLE HAVING HYDROPHOBIC LEAK PROTECTION ZONES

(75) Inventors: Carol L. Erdman, Duluth, GA (US); Harry J. Chmielewski, Brunswick, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/815,392

(22) Filed: Mar. 23, 2001

(65) Prior Publication Data

US 2002/138054 A1 Sep. 26, 2002

(51) Int. Cl.$^7$ .................................. A61F 13/15
(52) U.S. Cl. ............... 604/381; 604/381; 604/358; 604/378; 604/385.02; 604/375; 604/382; 604/385.101; 424/402
(58) Field of Search ................. 604/378, 381, 604/385, 375, 382, 385.101; 424/402

(56) References Cited

U.S. PATENT DOCUMENTS

| | | | |
|---|---|---|---|
| 4,050,462 A | 9/1977 | Woon et al. | |
| 4,300,562 A | 11/1981 | Pieniak | |
| 5,092,861 A | 3/1992 | Nomura et al. | |
| 5,098,423 A | 3/1992 | Pieniak et al. | |
| 5,558,655 A | 9/1996 | Jezzi et al. | |
| 5,597,906 A | 1/1997 | Wong et al. | |
| 5,643,588 A | * 7/1997 | Roe et al. .................. | 424/402 |
| 5,683,809 A | 11/1997 | Freeman et al. | |
| 5,817,079 A | 10/1998 | Bergquist et al. | |
| 5,830,201 A | 11/1998 | George et al. | |
| 5,885,266 A | 3/1999 | Chihani et al. | |
| 5,928,209 A | 7/1999 | Bodford et al. | |
| 5,935,118 A | 8/1999 | Gryskiewicz et al. | |
| 5,941,862 A | 8/1999 | Haynes et al. | |
| 5,945,175 A | 8/1999 | Yahiaoui et al. | |
| 5,990,377 A | 11/1999 | Chen et al. | |
| 6,017,336 A | 1/2000 | Sauer | |
| 6,040,251 A | 3/2000 | Caldwell | |
| 6,068,620 A | 5/2000 | Chmielewski | |
| 6,087,550 A | 7/2000 | Anderson-Fischer et al. | |
| 6,107,539 A | 8/2000 | Palumbo | |
| 6,114,596 A | 9/2000 | Nayak | |
| 6,117,121 A | 9/2000 | Faulks | |
| 6,120,488 A | 9/2000 | VanRijswijck et al. | |
| 6,120,783 A | 9/2000 | Roe et al. | |

\* cited by examiner

*Primary Examiner*—Rodney M. Lindsey
*Assistant Examiner*—Angela J Grayson
(74) *Attorney, Agent, or Firm*—Scott F. Yarnell; Christopher C. Campbell; Hunton & Williams

(57) ABSTRACT

An absorbent article that provides leakage protection and/or skin protection, as well as methods for using and preparing the absorbent article and novel compositions and composites for use in the absorbent article, is disclosed. The absorbent article comprises a permeable topsheet; a substantially impermeable backsheet; an absorbent core positioned between said permeable topsheet and said substantially impermeable backsheet; and a hydrophobic composition selectively disposed on the absorbent article to contain leakage. The hydrophobic composition is disposed at one or more leak protection zones.

74 Claims, 6 Drawing Sheets

ABSORBENT ARTICLE HAVING HYDROPHOBIC LEAK PROTECTION ZONES

FIELD OF THE INVENTION

This invention relates to the field of absorbent articles in general, and more particularly to absorbent articles that provide leakage protection and/or skin protection, as well as methods for using and preparing same, and novel compositions and composites for use in same.

BACKGROUND OF THE INVENTION

Disposable absorbent articles typically include a moisture-impervious backing sheet, an absorbent pad, and a liner sheet that contacts the body of a person wearing the article. In addition, elasticized regions are provided around the edges of the article to secure the article about the waist and legs of a wearer. Diapers typically further comprise opposed front and rear waist portions defining a waist opening, a crotch portion disposed there between, and a pair of elastically contractible leg openings along the side edges of the crotch portion. Disposable diapers having elasticized margins for placement about the legs of a wearer are disclosed in U.S. Pat. Nos. 4,050,462 and 5,092,861. An absorbent article having elasticized side margins and waist band margins are shown in U.S. Pat. No. 4,300,562.

Despite previous advancements in the field of absorbent articles, persons of ordinary skill in the art continue their efforts to produce more comfortable garments which are better able to contain urinary and fecal excretions. For instance, problems with prior diaper designs include leakage of urinary or fecal material from the garment. Prolonged contact of liquid or semi-solid excreta with the skin of the wearer is also a continuing problem in the art. For example, the moisture vapor and heat generated by the bodily exuded trapped within a diaper may lead conditions adjacent to wearer's skin which promotes skin irritation, infection, and the like. Although a plastic backsheet, as described above, is generally effective in precluding the passage of bodily exude outwardly, the backsheet is not efficient in preventing lateral leakage of liquids from the opposed side portions of the core sideward between the leg gathers of the backsheet and the wearer's skin. One solution to this problem, the tightening of leg gathers, presents problems in terms of the comfort of the baby and further skin irritation. Various other approaches had been attempted to address the lateral leakage of liquids from absorbent articles.

For example, U.S. Pat. No. 6,114,596 to Nayak et al. discloses a breathable diaper, feminine hygiene, or like disposable sanitary product having a cloth-like outer surface and including a plurality of materials from the skin-facing side outwardly, a topsheet, a core, an optional barrier, and a backsheet. The disclosed topsheet is formed of liquid- and vapor-permeable hydrophilic material, and the core is formed of highly absorbent material disposed outwardly of the topsheet for absorbing liquid received through the topsheet. The disclosed core has an inter surface in liquid communication with the topsheet and an outer surface. The disclosed optional barrier is formed for a multi-layer non-woven material which is hydrophobic and vapor-prominentable for limiting the outward escape of liquid therethrough while enabling the outward escape of heat and water vapor therethrough. The disclosed barrier has a base disposed adjacent the core outer surface. The disclosed backsheet is formed of a multi-layer non-woven material which is hydrophobic and vapor permeable for limiting the outward escape of liquid therethrough while enabling the outward escape of heat and water vapor therethrough. This backsheet is disclosed as being disposed at least partially as an outer surface of the diaper.

U.S. Pat. No. 6,017,336 to Sauer discloses an absorbent article which includes a pair of compression resistant containment barriers which are configured to inhibit the lateral flow of fecal exudates along the surface of the absorbent article. The containment barriers are disclosed as being laterally spaced apart to provide a void space between the wearer's back side and the surface of the absorbent article for containing body exudates. Each containment barrier is disclosed as defining a width to height ratio of at least about 0.5 and a compression resistance of at least about 50%. The absorbent article is disclosed as optionally including a containment dam which is located on the body facing surface of the absorbent article and which is configured to inhibit a longitudinal flow of fecal exudates along the surface of the absorbent article.

U.S. Pat. No. 5,597,906 to Roe, et al. discloses an absorbent article comprising a liquid pervious topsheet, a liquid pervious backsheet joined to at least a portion of the topsheet, an absorbent cord disposed between at least a portion of the topsheet and the backsheet, and a waste management element disposed in at least a portion of the crotch region. The waste management element preferably has an acceptance under pressure value of greater than about 0.50 grams of a viscous fluid bodily waste per square inch of the waste management element millijoule of energy input. The waste management element is also disclosed as having a storage under pressure values of at least about 0.70 grams of the viscous fluid bodily waste per square inch of the waste management element. The waste management element is also disclosed as optional having an Immobilization Under Compressed Inversion valve of greater than about 70% of the viscous fluid bodily waste accepted by the waste management element. The waste management is disclosed as being located anywhere in the article, including the crotch region.

U.S. Pat. No. 5,941,864 to Roe discloses a disposable absorbent article, such as a diaper having a first topsheet with apertures large enough for low-viscosity fecal material to pass through to a fecal material storage element. The fecal material storage element is disclosed as immobilizing the fecal material in position for dewatering, so that the liquid components of the fecal material are absorbed by the core and solid components of the fecal material are separated from the liquid components, to provide for easier-cleaning of the wearer when the soiled disposable absorbent article is removed.

U.S. Pat. No. 5,941,862 to Haynes et al. discloses absorbent structures comprising a first layer, a second layer juxtaposed in facing relation with said first layer, wherein at least one of the layers is fluid pervious. These structures are disclosed as having a continuous region between said first and second layers comprising hydrogel-forming polymer that is substantially uniformly distributed throughout the region. The continuous region is disclosed as at least partially surrounding multiple, spaced apart zones between said layers, which zones are substantially devoid of hydrogel-forming absorbent polymer. The first and second layers are disclosed as being bonded together such that said hydrogel-forming absorbent polymer is substantially immobilized when in dry state, an preferably at sites within plurality of the zones.

U.S. Pat. No. 5,558,655 to Jezzi et al. discloses in absorbent article, such as diaper, which comprises a composite structure of a "two-dimensional" or very flat, apertured film or nonwoven layer, in combination with a. fluid transferring layer and a superabsorbent polymer-containing laminate, and a absorbent core below the laminate to achieve superior dryness. The superabsorbent poylmer-containing laminate is disclosed as containing airlaid fibrous components and superabsorbent polymers and as swelling to at least three times its dry caliper upon fluid introduction in order to achieve movement of the coverstock away from the absorbent core which permits the coverstock to remain relatively dry and avoids rewetting.

U.S. Pat. No. 6,040,251 to Caldwell discloses barrier webs at a certain desirable physical qualities such as water resistance, increased durability, improved barrier qualities and the like. Barrier webs are disclosed as comprising a web that has been treated with a curable shear thinned thixotropic polymer composition which is adapted to be substantially impermeable to liquids, permeable to gases and impermeable to microorganisms. Further, the barrier webs are disclosed as being either impermeable to all microorganisms or impermeable to microorganisms of certain sizes. Also disclosed are fabrics that are capable of either selectively binding certain microorganisms, particles, or molecules depending upon what binding partners are incorporated into the polymer before application to the fabric.

U.S. Pat. No. 5,945,175 to Yahiaoui et al discloses a coated porous substrate composed of a hydrophobic polymer which is substantially uniformly coated with a hydrophilic polymeric material. The substrate may be a sheet-like material, examples of which are forms, fibers, and fibrous webs. The fibrous webs are disclosed as desirably being nonwoven webs. The coating on the substrate is disclosed as being durable to an aqueous medium at a temperature in a range of from about 10° C. to about 50° C. and does not significantly suppress the surface tension of an aqueous medium-with which the coated substrate may come in contract. The hydrophobic polymer is disclosed as being a polyolefin, such as polyethylene or polypropylene. The hydrophilic polymeric material is disclosed as being a polysaccharide or a modified polysaccharide.

U.S. Pat. No. 6,117,121 to Faulks et al. discloses an absorbent article including an absorbent core located between a bodyside liner and an outer cover. The absorbent article is disclosed as having a leg cuff mounted to a base structure in the crotch portion thereof. The leg cuffs are disclosed as being partially stretched when attached to respective longitudinal side portions near the crotch portion of the absorbent article.

U.S. Pat. No. 6,107,539 to Palumbo et al. discloses disposable absorbent articles comprising a backsheet, a topsheet, a fluid acquisition/distribution region and at least one fluid storage region, said article having a total product acquisition performance of more than 3.75 ml/sec in the first gush and more than 0.5 ml/sec in the fourth gush and an in bag stack height of less than 9.9 mm, characterized in that said topsheet allows it to retain no more then 0.25 g of fluid as measured by the topsheet-on-acquisition-material-wetness test, and that said acquisition/distribution region has a drip capacity of at least 5.0 grams of fluid per gram of material.

U.S. Pat. No. 5,935,118 to Gryskiewicz et al. discloses an absorbent article that includes a garment shell and at least one liquid containment beam formed of an absorbent material. The liquid containment beam has an attachment edge bonded to the garment shell so that the containment beam can lie against the garment shell and also pivot about an axis defined by the attachment edge. For comfort during use, the containment beam desirably has a width to thickness ratio of at least about 3:1. In particular embodiments, the absorbent article includes pairs of inner and outer containment beams, with the inner containment beams adapted to lie against the garment shell and the outer containment beams adapted to lie against the inner containment beams.

U.S. Pat. No. 6,087,550 to Anderson-Fischer et al. relates to water responsive thermoplastic compositions and articles constructed thereof. This invention particularly relates to thermoplastic copolyester compositions useful for the manufacture of disposable articles such as disposable diapers and feminine napkins. More particularly, this invention relates to thermoplastic copolyester compositions that are useful as a raw material in the manufacture of nonwovens, barrier films or coatings, as well as for various improved hot melt adhesive compositions useful for incorporating hydrophilic features into disposable articles.

U.S. Pat. No. 6,120,783 to Roe et al. discloses web materials which have two or more skin care compositions disposed thereon. The skin care compositions are transferable to the wearer's skin by normal contact and/or wearer motion and/or body heat. The skin care compositions disclosed in the present invention are selected to maintain and/or improve the skin health of the wearer upon transfer during use, for example, to provide a skin protective barrier or a therapeutic benefit; to minimize the abrasion between the cuffs and skin in the area where the cuffs contact the wearer's skin, resulting in less skin irritation; to improve BM clean up on the skin, or to improve the barrier properties of the cuffs. Web materials of the present invention have a wide range of potential uses in both durable and disposable articles, but are particularly well suited for use in disposable absorbent articles such as disposable diapers, incontinent briefs, training pants, sanitary napkins, and the like.

U.S. Pat. No. 5,683,809 to Freeman et al. discloses protective articles such as diapers, having filmless hydrophobic barrier elements such as cuffs and backing sheets. The barrier cuffs—which can be, for instance, leg cuffs and waistbands—and the backing sheets can be provided from fabrics having a fabric weight of at least 10 gsy.

U.S. Pat. No. 5,928,209 to Bodford et al. discloses a breathable diaper, feminine hygiene, or like disposable sanitary product construction includes a plurality of materials including, from the skin-facing side outwardly, a topsheet of liquid- and vapor-permeable hydrophilic material. A core of highly absorbent material is disposed outwardly of the topsheet for absorbing fluid received through the topsheet, the core having an inner surface in fluid communication with the topsheet. A backsheet is disposed at least partially as an outer surface of the construction and is formed of a pouch defined by two layers of a non-woven hydrophobic and vapor-permeable material, with absorbent or superabsorbent particles therebetween, so that the backsheet limits the outward escape of liquid therethrough while enabling the outward escape of heat and water vapor therethrough. Each backsheet layer is an at least two-layer spunbound-meltblown SM or an at least three-layer spunbond-meltblown-spunbond SMS.

U.S. Pat. No. 5,990,377 to Chen et al. discloses a dual-zoned, three-dimensional, resilient absorbent web is disclosed which is suitable as body-side liner for absorbent articles such as feminine pads, diapers and the like. When used as a liner in absorbent articles, the dual-zoned web combines the advantages of apertured films and soft, nonwoven cover layers in one structure while still being inherently hydrophilic. The liner comprises a web of wet-resilient, hydrophilic basesheet having a three-dimensional topography comprising elevated regions onto which hydrophobic matter is deposited or printed and a plurality of spaced apart depressed regions. In a preferred embodiment, the hydrophobic matter applied to the elevated regions of the basesheet comprises hydrophobic fibers in a contiguous nonwoven web which has been apertured or provided with slits or other openings, such that the apertures or openings overlay a portion of the depressed regions. The elevated hydrophobic regions enhance dry feel and promote fluid flow toward the lower hydrophilic regions, which comprise the exposed depressed regions of the basesheet. The basesheet is preferably in liquid communication with underlying absorbent material, most preferably a stabilized airlaid cellulosic material or compressed stabilized fluff such that the absorbent material can wick fluid out of the basesheet by capillary action. When soft, hydrophobic fibers are deposited on the elevated regions, the liner also has a soft, cloth-like feel in addition to a dry feel in use.

U.S. Pat. No. 6,120,488 to VanRijswijck et al. discloses an absorbent article, such as a diaper, containing cuffs and a topsheet with one or more skin care compositions disposed thereon. The skin care compositions are transferable to the wearer's skin by normal contact and/or wearer motion and/or body heat. The skin care compositions disclosed in-the present invention are selected to maintain and/or improve the skin health of the wearer upon transfer during use, for example, to provide a skin protective barrier or a therapeutic benefit; to minimize the abrasion between the cuffs and skin in the area where the cuffs contact the wearer's skin, resulting in less skin irritation; to improve BM clean up on the skin, or to improve the barrier properties of the cuffs.

U.S. Pat. No. 5,817,079 to Bergquist et al. discloses in absorbent products, such as sanitary napkins, discreet areas of dry fibrous materials such as fluidrepellent materials are precisely placed in various planes within the product so as to provide barriers to bodily fluid leakage from the product. In a preferred embodiment, hydrophobic fibers are placed around the periphery of a central absorbent area of an absorbent product to discourage and/or prevent side or end leakage from the product.

U.S. Pat. No. 5,830,201 to George et al. discloses a flushable diaper for use on the body of an infant or adult. An envelope has inner and outer walls which are secured together at their outer periphery to form an inner cavity. The outer wall is comprised of a hydrophobic outer layer together with a hydrophilic inner layer. The inner wall is comprised of a hydrophobic outer layer together with a hydrophilic inner layer. The inner and outer walls are separated by an interior cavity which contains one or more containers. The container is comprised of either a single layer or a laminated wall which forms a chamber that encloses a charge of water. The laminated wall is comprised a hydrophobic inner laminate and a hydrophilic outer laminate. When manually ruptured, the containers release water into the double walled envelope, which causes disintegration of the hydrophilic inner layers of the double walls, along with the hydrophobic outer layers. An absorbent member is carried on the inner wall of the envelope, and the absorbent member comprises a fluid pervious cover which encloses an inner body that is comprised of a material which is sufficiently hydrophilic to absorb urine and other fluids from the body while maintaining structural integrity of the inner body and to also absorb water in an effective amount to cause the inner body to disintegrate into small pieces.

U.S. Pat. No. 5,885,266 to Chihani et al. discloses an absorbent article such as a diaper, an incontinence guard or a sanitary napkin includes a liquid-permeable outer sheet, a liquid-impermeable bottom sheet and an absorbent body placed therebetween. The outer sheet and the absorbent body are at least partially joined together with a hydrophilic glue.

As is apparent from the foregoing, each of the prior references present a variety of means for controlling leakage in absorbent garments. However, all of these proposed means are deficient in terms of effectiveness and low product quality, mechanical complexity in design, and/or associated cost inefficiencies.

In view of the deficiencies of the various products and processes disclosed in the above discussed references, it is highly desirable to provide cost-efficient absorbent articles that display superior leak protection, as well as novel compositions and composites for use in said absorbent articles. Further, it is highly desirable to provide a cost-efficient process for producing absorbent articles having superior leak protection. Moreover, it is also highly desirable to provide cost-efficient absorbent articles, and methods for preparing such articles, that confer secondary benefits of skin wellness to the users of said articles, in addition to superior leak protection.

SUMMARY OF THE INVENTION

The present invention provides cost-efficient absorbent articles, and novel compositions and composites for use in same, that display unexpectedly superior leak protection. Further, the present invention provides a cost-efficient process for producing absorbent articles having superior leak protection. Moreover, the present invention provides cost-efficient absorbent articles, methods for preparing and using such articles, and novel compositions and composites for use in same, that confer secondary benefits of skin wellness to the users of said articles in addition to superior leak protection.

One embodiment of the present invention is an absorbent article comprising: a permeable topsheet; a substantially impermeable backsheet; an absorbent core disposed between said permeable topsheet and said substantially impermeable backsheet; and a hydrophobic composition selectively disposed between the skin-opposing surface of the substantially impermeable backsheet and the skin of a wearer of the absorbent article to contain leakage.

A further embodiment of the present invention is an absorbent article comprising: a permeable topsheet; a substantially impermeable backsheet; an absorbent core disposed between said permeable topsheet and said substantially impermeable backsheet; and a hydrophobic composition disposed between the skin-opposing surface of the substantially impermeable backsheet and the skin of a wearer of the absorbent article at a leak protection zone or plurality of leak protection zones; wherein said hydrophobic composition comprises a hydrophobic substance effective for skin protection, a substance effective for skin care, a substance effective for skin wellness, a substance effective for skin improvement, a substance perceived as having a skin wellness benefit or combinations thereof.

A still further embodiment of the present invention is an absorbent garment comprising: a front waist portion and a rear waist portion cooperating to form a waist opening; a crotch region formed between said front waist portion and said rear waist portion; a pair of leg openings on opposed sides of the crotch region; a permeable topsheet, a substantially impermeable backsheet and an absorbent core positioned between said topsheet and said backsheet; and a hydrophobic composition disposed on said permeable topsheet at a leak protection zone or plurality of leak protection zones.

An even further embodiment of the present invention is an absorbent article comprising: a permeable topsheet; a substantially impermeable backsheet; an absorbent core disposed between the permeable topsheet and the substantial impermeable backsheet; a tissue layer disposed between the absorbent core and the permeable topsheet; and a hydrophobic composition disposed on said tissue layer at a leak protection zone or plurality of leak protection zones.

Another embodiment of the present invention is a method for preparing an absorbent article comprising: identifying a leak protection zone or a plurality of leak protection zones; disposing a hydrophobic composition at one or more predetermined areas on a substrate; and forming an absorbent article comprising the substrate such that the one or more predetermined areas correspond to the leak protection zone or plurality of leak protection zones.

Yet another embodiment of the present invention is a method for preparing an absorbent article comprising: disposing a hydrophobic composition at predetermined areas on a tissue layer or a permeable topsheet; and forming said tissue layer or permeable topsheet into an absorbent core such that the predetermined areas correspond to a leak protection zone or a plurality of leak protection zones.

Still another embodiment of the present invention is a composition in an absorbent article for providing leak protection and/or skin wellness comprising: an effective amount of a hydrophobic substance selected from the group consisting of cocoa butter, petrolatum, dimethicone, a zinc oxide preparation, beeswax, lanolin, jojoba oil and combinations thereof effective in providing leak protection when selectively disposed at a leak protection zone or plurality of leak protection zones on said absorbent article.

DETAILED DESCRIPTION OF THE INVENTION

As used herein, the term "absorbent article" refers to articles that absorb and contain exudates, and more specifically refers to articles which are placed against or in proximity to the body of a wearer of the absorbent article to absorb and contain various exudates discharged from the body. A non-exhaustive list of examples of absorbent articles includes diapers, diaper cores, diaper covers, disposable diapers, training pants, feminine hygiene products and adult incontinence products. The term "disposable article" refers to absorbent articles that are intended to be discarded or partially discarded after a single use, i.e., they are not intended to be laundered or otherwise restored or reused. The term "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. The employance of thin, comfortable garments is disclosed, for example without limitation in U.S. Pat. No. 5,098,423 to Pineiak et al. which is herein incorporated by reference.

The present invention provides an absorbent article, as well as a method of preparing same and a method of using said absorbent article, having unexpectedly superior properties of absorbency, leakage protection and/or skin wellness. The present invention can be understood by the disclosure herein and/or by reference to the drawings.

Figure 1:
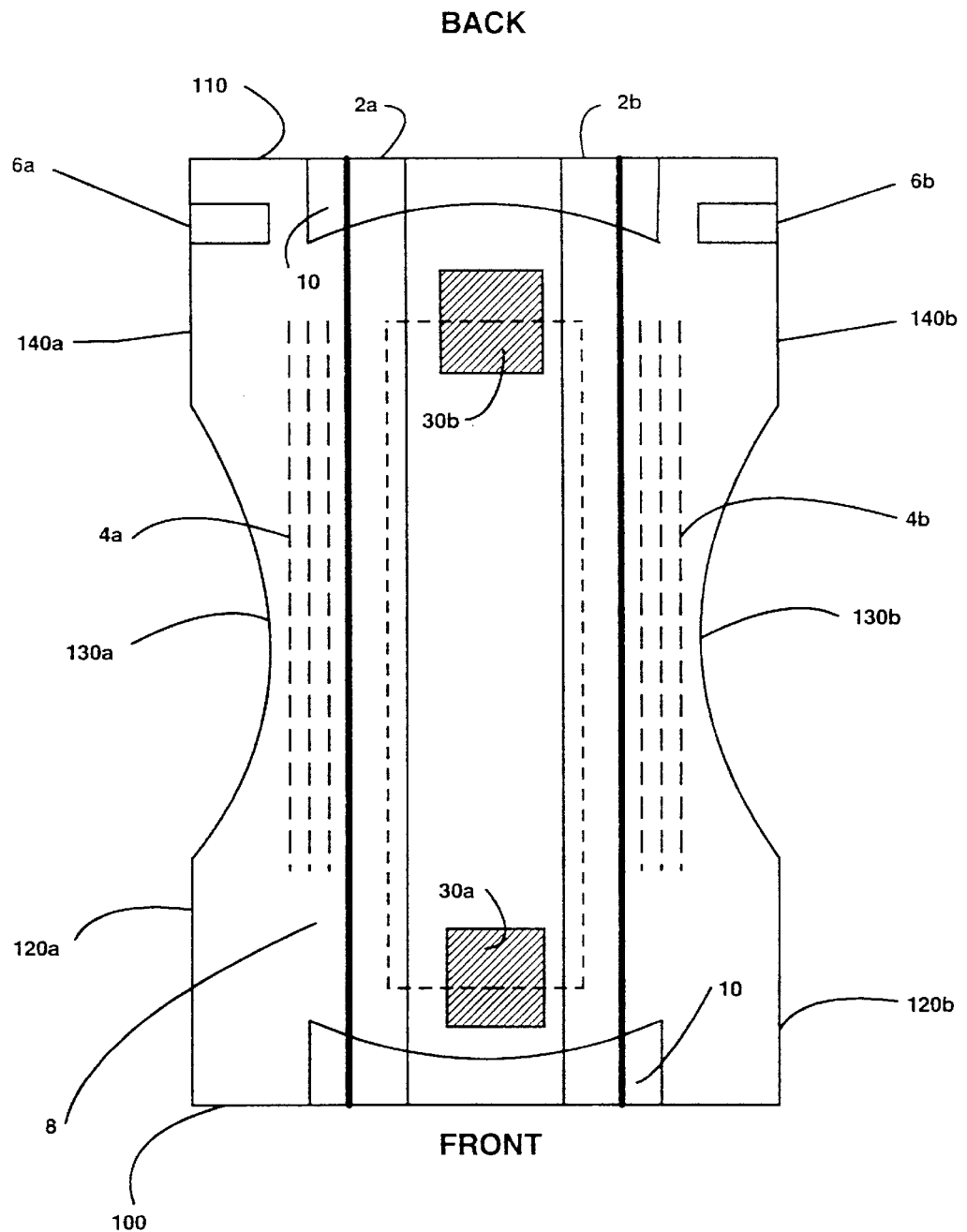
FIG. 1 is a topsheet perspective of an absorbent article in accordance with an implementation of the present invention.

Referring to FIG. 1, an absorbent article (e.g., a diaper) is shown from a topsheet perspective. The absorbent article comprises a front edge 100, a back edge 110, two front side edges 120a and 120b, two back side edges 140a and 140b, and two leg cutout edges 130a and 130b, position such that leg cutout edge 130a is disposed between front side edge 120a and back side edge 140a, and leg cutout edge 130b is disposed between front side edge 120b and 140b.

Referring still to FIG. 1, the absorbent article further comprises two inner leg gathers 2a and 2b, each of which extends longitudinally along the topsheet of the absorbent article from the back edge 110 to the front edge 100. The inner leg gathers 2a and 2b are approximately parallel to one another and are each positioned approximately parallel to the front and back side edges 120a, 120b, 140a and 140b in the longitudinal direction of the absorbent article. Further, each inner leg gather is located adjacent to and inward of the inner most portion of the leg cutout edges 130a and 130b.

Referring still to FIG. 1, the absorbent article further comprises two leg elastics 4a and 4b, each of which is positioned approximately adjacent and parallel to each of the inner leg gathers 2a and 2b. Each of the leg elastics is located outward of said inner leg gathers 2a and 2b. Two fasteners 6a and 6b are each located at or near the back side edge of the absorbent article. An absorbent core 8 is shown as being disposed between the topsheet 40 and a substantially impermeable backsheet 50 (not shown in FIG. 1). The absorbent core 8 is positioned longitudinally along the absorbent article. Waist foam 10 is optionally present in the absorbent article and positioned near and adjacent to the front edge 100 and/or back edge 110, on the skin-facing surface of the topsheet 40.

As shown in FIG. 1, a pair of leak protection zones 30a and 30b are shown, with a first leak protection zone 30a being located on the topsheet 40 adjacent to and inward of the front edge 100 and positioned centrally between the two inner leg gathers 2a and 2b. A second leak protection zone 30b is located near the back edge disposed centrally between the two inner leg gathers 2a and 2b. Each said leak protection zone 30a and 30b is defined as an approximately rectangular area. Each leak protection zone 30a and 30b comprises a hydrophobic composition disposed on and/or within the permeable topsheet 40. The hydrophobic composition may totally or partially cover the leak protection zone. The illustration of the two leak protection zones is merely illustrative. The present invention also contemplates the presence of one or more than two leak protection zones, as well as two leak protection zones.

At each leak protection zone, the hydrophobic composition is disposed on the topsheet (as shown in the figure), the flat tissue, the backsheet, the polymer barrier and/or another component of the absorbent article that is positioned near or attached to the foregoing and is disposed between the skin-opposing surface of the backsheet and the skin of the wearer of the absorbent article, as well as on or disbursed at any combinations of the foregoing absorbent article components.

Figure 2:
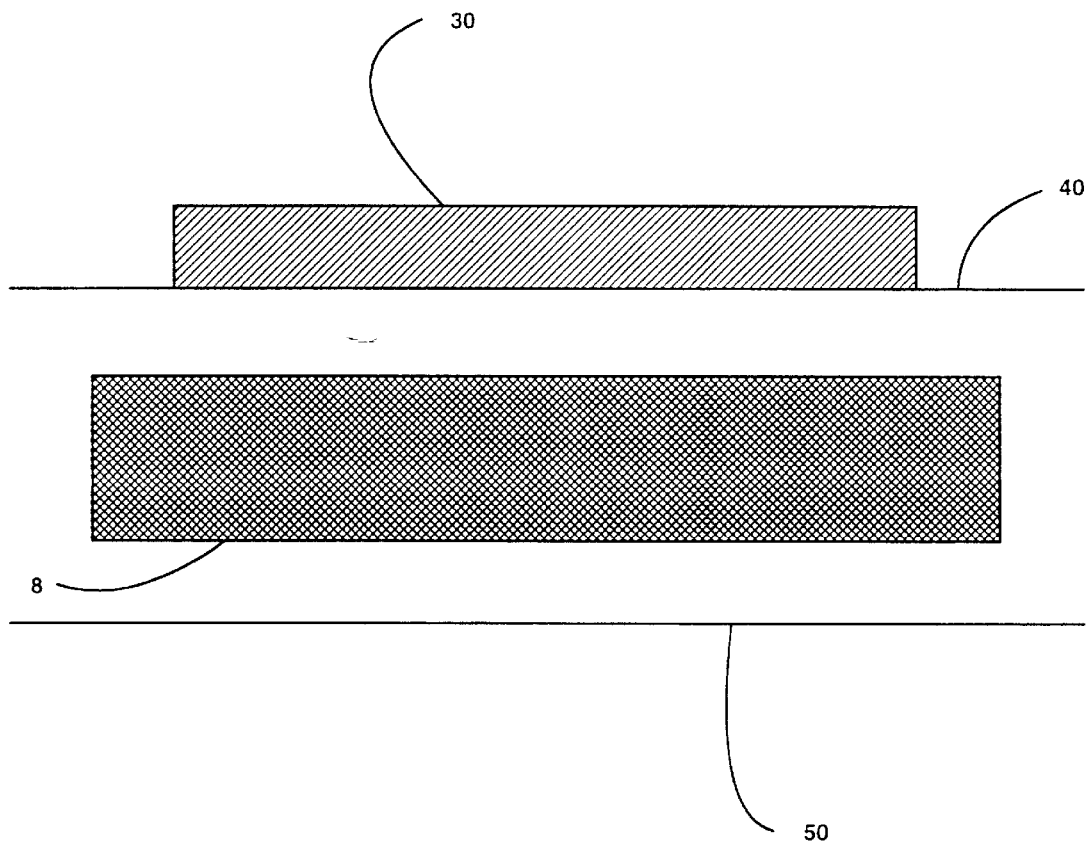
FIG. 2 is a cross-sectional view of an absorbent article in accordance with an implementation of the present invention.

Referring to FIG. 2, a cross-sectional view of an absorbent article in accordance with one implementation of the present invention is shown. In particular, FIG. 2 depicts a cross-sectional view of an absorbent article as it would be viewed from the front or back of the absorbent article. The absorbent article comprises a permeable topsheet 40, a substantially impermeable backsheet 50, an absorbent core 8 that is disposed between said permeable topsheet 40 and said substantially impermeable backsheet 50, and leak protection zones 30a and 30b disposed on a section of said permeable topsheet 40. Each of the leak protection zones 30a and 30b is disposed on the skin-facing surface of the permeable topsheet 40 (e.g., the surface opposite the surface on the permeable topsheet 40 that faces the absorbent core 8). Each leak protection zone 30a and 30b comprises a hydrophobic composition. The hydrophobic composition may partially or totally cover one or both of the leak protection zones 30a and 30b.

Figure 3:
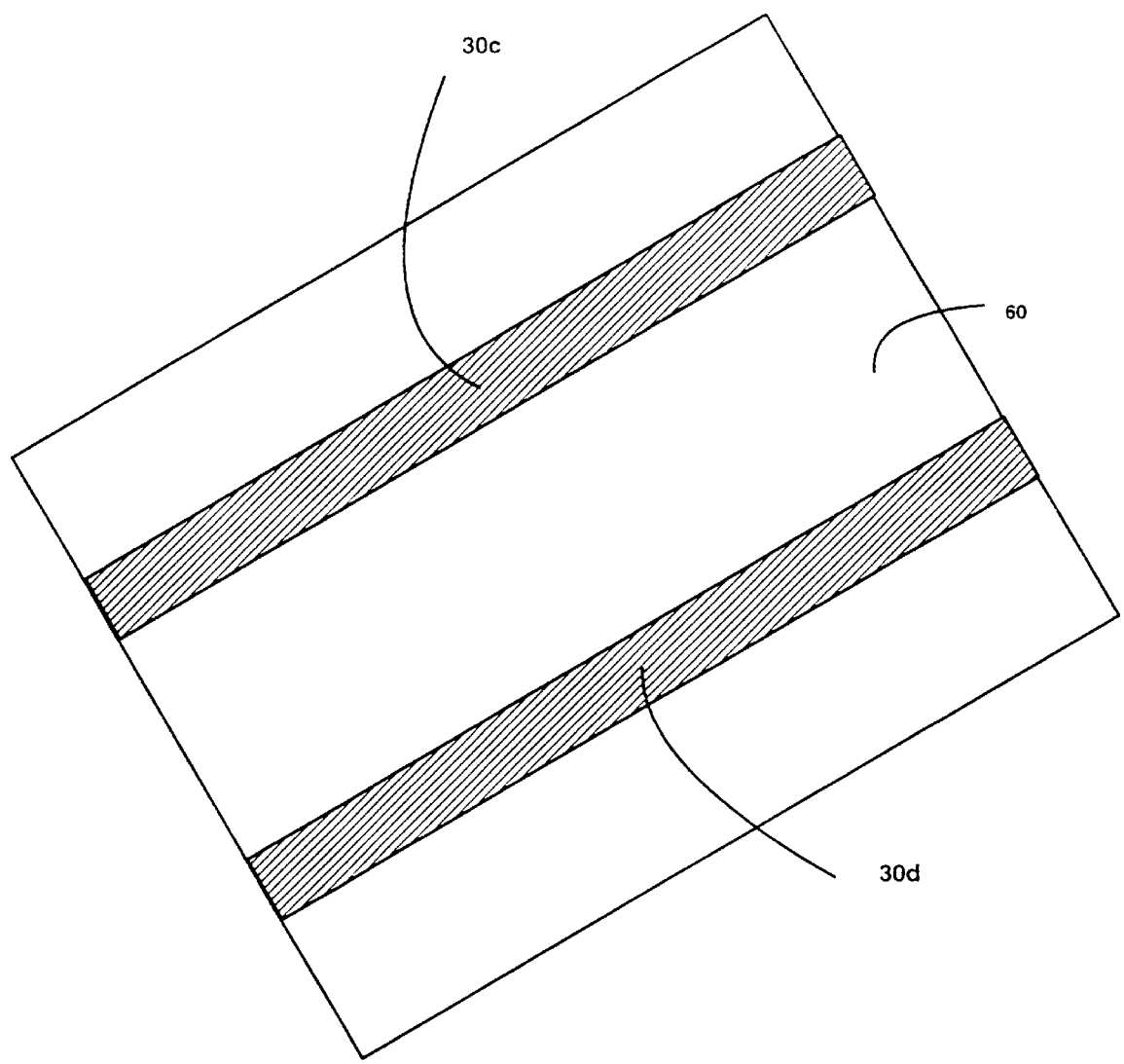
FIG. 3 is a plan view of flat tissue before being used to wrap an absorbent core of an absorbent article in accordance with an implementation of the present invention.

FIG. 3 is a plan view of flat tissue before being used to wrap an absorbent core of an absorbent article in accordance with an implementation of the present invention. Referring to FIG. 3, flat tissue 60 as it would appear prior to lapping the absorbent core is depicted. As shown in FIG. 3, two leak protection zones 30c and 30d, in accordance with one implementation of the present invention, are located on the flat tissue at two sites running longitudinally along the surface of the flat tissue 60 parallel to the side edges of the flat tissue 60 from the front to the back of the flat tissue 60. The leak protection zones 30c and 30d are each comprised of a hydrophobic composition adhered to the flat tissue 60 and partially or totally covering leak protection zones 30a and 30b.

Figure 4:
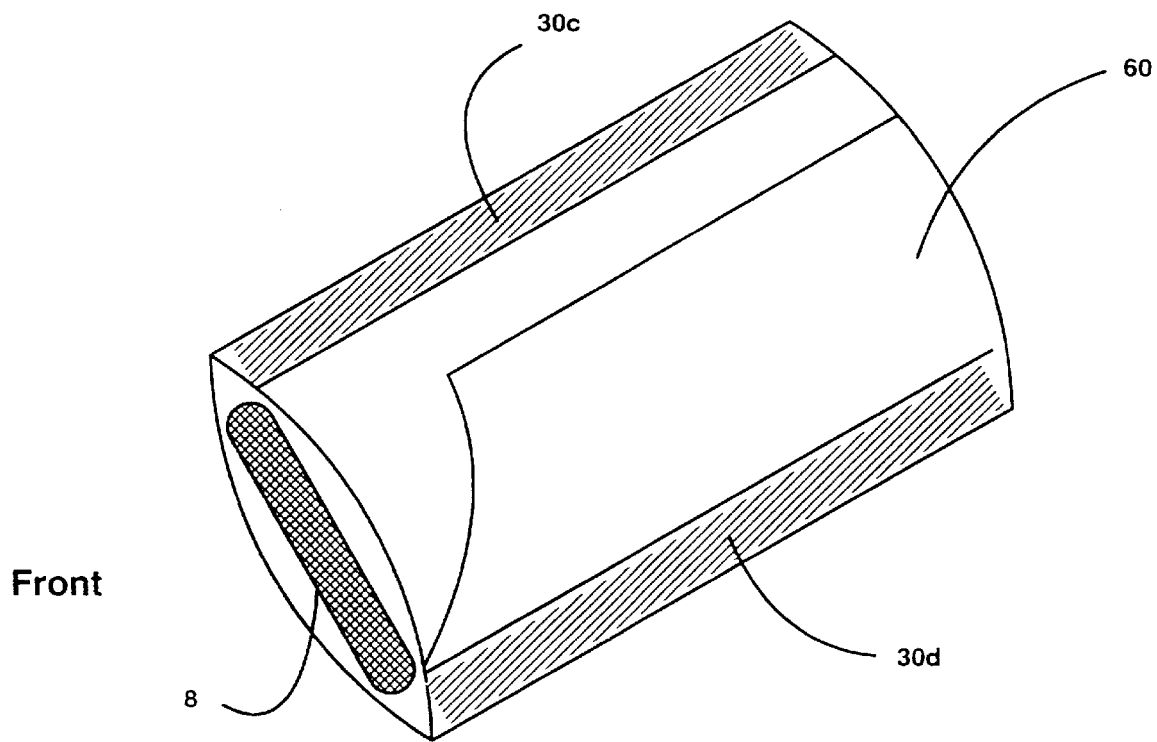
FIG. 4. is a cross-sectional view of the flat tissue wrapping an absorbent core in an absorbent article in accordance with an implementation of the present invention.

FIG. 4. is a cross-sectional view of the flat tissue wrapping an absorbent core in an absorbent article in accordance with an implementation of the present invention. Referring to FIG. 4, an absorbent core of an absorbent article in accordance with one embodiment of the invention is shown being wrapped by the flat tissue 60 which forms a tissue layer around the absorbent core 8. Leak protection zones 30c and 30d are disposed at or near the side edges of the absorbent core 8 which run longitudinally from about the front edge to about the back edge of the absorbent core, said front edge of the absorbent core corresponding to the front edge 100 of the absorbent article and said back edge 110 of the absorbent article. Each leak protection zone 30c and 30d is partially or totally comprised of a hydrophobic composition adhered to the flat tissue 60. In accordance with this implementation of the invention, leak protection zones 30c and 30d provide a barrier to prevent or substantially inhibit leakage of moisture from the long edges of the absorbent core 8 to provide an absorbant article having unexpectedly superior properties of absorbency and/or leakage protection.

Figure 5A:
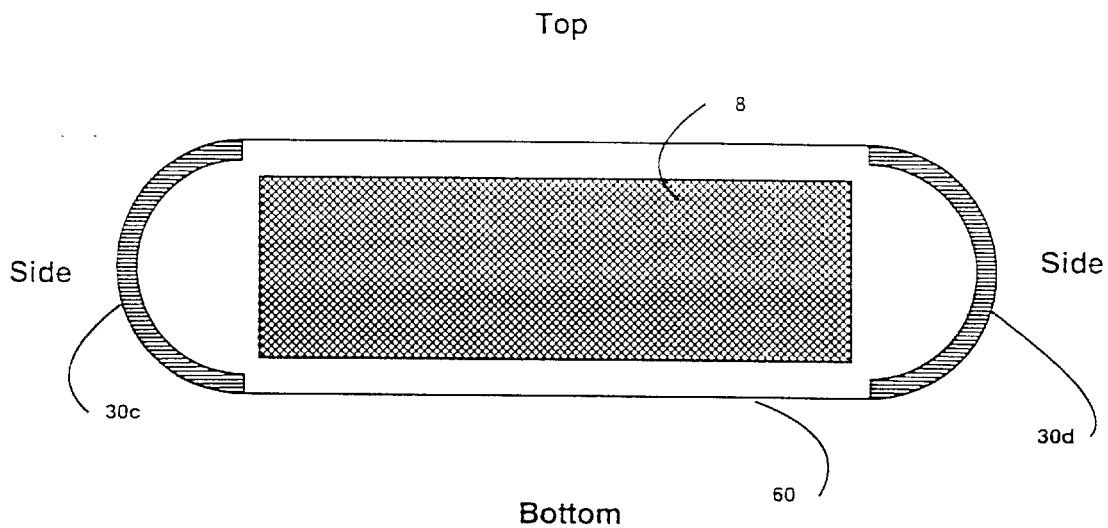
FIGS. 5A and 5B are cross-sectional front views of absorbent cores wrapped by tissue layers in absorbent articles in accordance with implementations of the present invention.

FIG. 5A is a cross-sectional front view of an absorbent core wrapped by tissue layers in an absorbent article in accordance with an implementation of the present invention. Referring to FIG. 5A, a cross-sectional view of an absorbent article in accordance with one implementation of the present invention, as shown from the front of the absorbent article, is depicted. An absorbent core 8 is disposed adjacent to the inner surface of flat tissue 60. A pair of leak protection zones 30c and 30d are disposed on the flat tissue 60 on the surface of said flat tissue 60 opposite the surface facing the absorbent core 8. Each of the leak protection zones 30c and 30d is located at a portion of the flat tissue 60 approximately corresponding to the side edges of the absorbent article. Optionally, each of the leak protection zones 30c and 30d is located on the inside surface and/or the outside surface of the flat tissue 60.

Figure 5B:
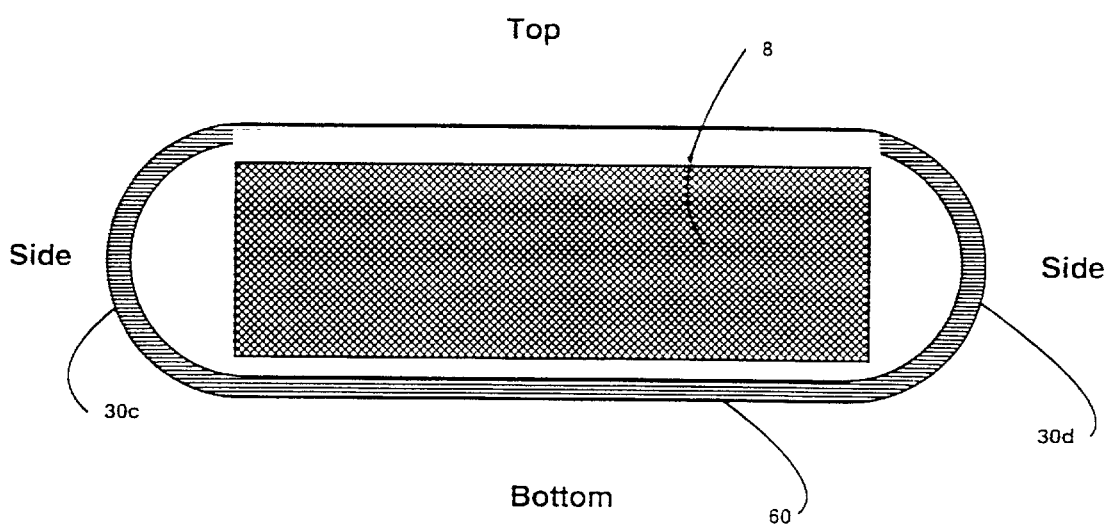

FIG. 5B is a cross-sectional front view of an absorbent core wrapped by tissue layers in an absorbent article in accordance with an implementation of the present invention. Referring to FIG. 5B, a cross-sectional view of an absorbent article in accordance with one implementation of the present invention, as shown from the front of the absorbent article, is depicted. An absorbent core 8 is disposed adjacent to flat tissue 60. A leak protection zone is depicted as being disposed on the flat tissue 60 on the surface of said flat tissue 60 opposite the surface facing the absorbent core 8 (e.g., the skin-opposing surface of the flat tissue 60). The leak protection zones 30c and 30d are disposed about the flat tissue 60 continuously at portions corresponding to the sides of absorbent core 8 and the substantially impermeable backsheet 50. The leak protection zones are optionally located on the inside surface and/or the outside surface of the flat tissue 60.

In an implementation of the present invention, the hydrophobic composition is optionally selectively disposed on and/or within the permeable topsheet 40 and/or the flat tissue 60. The hydrophobic composition may be disposed on one surface or both surfaces of each of the permeable topsheet 40 or flat tissue 60. In another implementation of the present invention, the hydrophobic composition is optionally selectively disposed on a layer or component of the absorbent article adhered to and/or adjacent to a surface of the permeable topsheet 40 and/or flat tissue 60.

Figure 6:
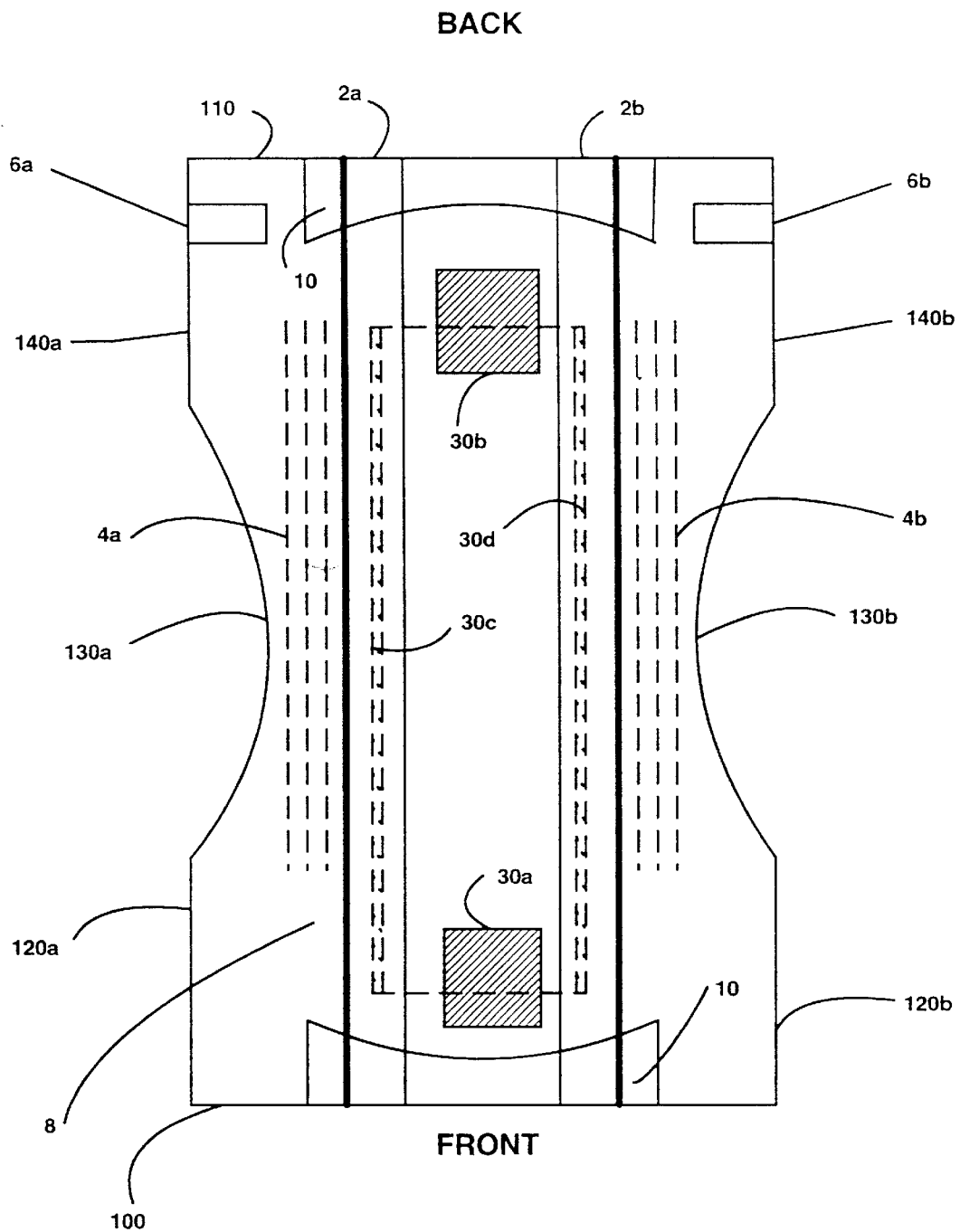
FIG. 6 is a topsheet perspective of an absorbent article in accordance with an implementation of the present invention.

As shown in FIG. 6, in accordance with an implementation of the present invention, leak protection zones 30a and 30b are located on the permeable topsheet 40 and leak protection zones 30c and 30d are located on a tissue layer 60 disposed centrally between said permeable topsheet 40 and the absorbent core 8. Optionally, a first leak protection zone 30a on said permeable topsheet is located near the front edge 100 of the absorbent article and between said inner leg gathers 2a and 2b, and a second leak protection zone 30b is located near the back edge 110 of the absorbent article disposed centrally between the inner leg gathers 2a and 2b. Further, a third leak protection zone 30c is located longitudinally along the side edge of the flat tissue 60 that is disposed between the absorbent core 8 and permeable topsheet 40, and a fourth leak protection zone 30d is located longitudinally on the surface of the tissue layer 60 facing the topsheet 40 approximately corresponding to a side edge of the absorbent core 8, said side edge corresponding to a side edge of said absorbent article.

The absorbent core may be of any desirable shape. Non-limiting exemplary shapes of absorbent cores in accordance with the present invention include a rectangular shape, a substantially rectangular shape, a T shape, an hour glass shape, or combinations thereof. Preferably, the absorbent core is a rectangular shape.

The hydrophobic composition comprises one or more hydrophobic substances or a combination of substances that, when combined, provide hydrophobic properties of moisture repulsion, as generally defined. A hydrophobic substance is any substance displaying hydrophobic properties of moisture repulsion, as generally defined. Further, the hydrophobic substance may be a skin-friendly substance. A skin-friendly substance, as referred to herein, includes substances effective for skin protection, skin care, skin wellness, skin improvement, substances generally perceived as having a skin wellness benefit or combinations thereof, for example without limitation. Persons of ordinary skill in the art would readily be able to identify and select such substances for use in implementations of the present invention, based upon the disclosure herein.

Preferably, the hydrophobic substance of the present invention is selected from the group consisting of theobroma oil, cacao butter, cocoa butter, petrolatum, mineral jelly, white mineral oil, dimethicone, zinc oxide preparation, beeswax, lanolin, jojoba oil, chinese white, zinc white and combinations thereof. More preferably, the hydrophobic substance is selected from the group consisting of petrolatum, dimethicone, jojoba oil, and cocao butter. Even more preferably, the hydrophobic substance is cocoa butter.

The hydrophobic composition (i.e., hydrophobic substance or combination of hydrophobic substances) may be uniform within a leak protection zone or may be independently varied within each leak protection zone. For example, in one implementation of the present invention, a first leak protection zone may be partially covered by dimethicone and partially covered by a zinc oxide preparation, without limitation. The dimethicone and zinc oxide compositions may overlap, partially overlap or be entirely independent of one another, without limitation.

Where multiple leak protection zones are present in an absorbent article, in accordance with an implementation of the present invention, the hydrophobic composition of each leak protection zone may comprise the same substance or combination of substances, or one or more leak protection zones may comprise a different substance or combination of substances. For example, in accordance with one implementation of the present invention, an absorbent article may comprise a first leak protection zone comprising cocoa butter and a second leak protection zone comprising zinc oxide preparation, without limitation. In another implementation of the present invention, for example, an absorbent article may comprise a first leak protection zone comprising dimethicone and zinc oxide preparation and a second leak protection zone comprising only zinc oxide preparation or only petrolatum, without limitation.

The hydrophobic composition may comprise one or more skin-friendly substances and/or substances perceived as being skin-friendly. The skin-friendly substance or substances may be one or more of the hydrophobic substances or an additive, without limitation.

The hydrophobic composition may comprise any additive, such as a skin-friendly substance, a substance perceived as having a skin wellness benefit or a combination of substances that when combined are beneficial and/or perceived as being beneficial to the skin of a wearer of the absorbent article of the present invention. Skin-friendly substances used as additives include substances effective for skin protection, substances effective for skin care, substances effective for skin wellness, substances effective for skin improvement, substances perceived as having a skin wellness benefit or combinations thereof, without limitation. Such a substance or combination of substances may be such that alone or in combination with other additives it has a beneficial effect on the skin of the wearer. Alternatively, the additive may be such that in combination with the hydrophobic substance or hydrophobic substances it provides beneficial effects and/or perceived beneficial effects for the skin of the wearer. Persons of ordinary skill in the art would be readily able to identify and select such substances, as described above, for use in implementations of the present invention, based upon the disclosure herein.

Other additives, such as stabilizers, excipients, colorants, fragrances and the like, are also contemplated by the present invention. Persons of ordinary skill in the art would be readily able to identify and select such additives for use in implementations of the present invention, based upon the disclosure herein.

As shown in the figures and described above, the hydrophobic composition is selectively disposed at a leak protection zone or plurality of leak protection zones. The composition is disposed between the skin-opposing surface of the substantially impermeable backsheet and the skin of the wearer of the absorbent article. For example, the hydrophobic composition may be disposed directly on and/or within the permeable topsheet, the skin-facing surface of the substantially impermeable backsheet, absorbent core and/or tissue layer or layers and/or indirectly on the foregoing (e.g., by means of an additional component or components attached to, partially attached to, and or near any of the foregoing components), without limitation.

A leak protection zone may be defined by a plurality of contact points on said permeable topsheet, backsheet, absorbent core, tissue layer, additional component and/or any combination. For example, in one implementation of the present invention, the hydrophobic composition is in contact with a portion of said permeable topsheet corresponding to the waist area of a wearer of said absorbent article and/or a portion of the tissue layer disposed between the absorbent core and the permeable topsheet, without limitation. In a further implementation of the present invention, the hydrophobic composition is disposed between the skin-opposing surface of the backsheet and the skin of a wearer of the absorbent article, but the hydrophobic composition is not in contact with a portion of the permeable topsheet and/or the tissue layer. Any variation or combination of the foregoing examples may be optionally employed in accordance with various implementations of the present invention, as would be readily appreciated by persons of ordinary skill in the art.

Preferably, the hydrophobic composition is in contact with a portion of said permeable topsheet corresponding to the waist area of a wearer of said absorbent article and/or a portion of the tissue layer disposed between the absorbent core and the permeable topsheet.

In one implementation of the present invention, the leak protection zone may defined on one side by the front or back perimeter of the permeable topsheet or by a line substantially parallel to said front or back perimeter of the permeable topsheet at a predetermined distance from said perimeter. Optionally, the leak protection zone is defined by outside and inside opposing edges substantially parallel to the front and back perimeter of the permeable topsheet. Each leak protection zone is preferably transversely centered such that the center of each leak protection zone substantially corresponds to a mid-line that dissects the absorbent article in the longitudinal direction into two even halfs.

Preferably, each leak protection zone is defined by outside and inside opposing edges substantially parallel to the front and back perimeter of the permeable topsheet and located at a predetermined distance from said front and back perimeter. More preferably, each leak protection zone is defined by outside and inside opposing edges substantially parallel to the front and back perimeter of the permeable topsheet, said outside opposing edge of each leak protection zone being about 0.25 mm to about 20 mm from the nearest said perimeter of the permeable topsheet. Even more preferably, each leak protection zone is defined by outside and inside opposing edges substantially parallel to the front and back perimeter of the permeable topsheet, said outside opposing edge of each leak protection zone being about 2 mm to about 10 mm from the nearest said perimeter of the permeable topsheet. Each leak protection zone is optionally defined on an outside opposing edge by a first line substantially parallel to the front or back perimeter of the permeable topsheet and on an inside opposing edge by a second line substantially parallel to said outside opposing edge of the leak protection zone, said first line being about 100 mm from said second line.

The hydrophobic composition may be of various sizes and shapes on the permeable topsheet that are effective in providing leak protection. Preferably, the hydrophobic composition forms a substantially rectangular area of about 100 mm to about 120 mm in width and about 35 mm to about 45 mm in length on the permeable topsheet. More preferably, the hydrophobic composition forms a substantially rectangular area of about 50 to about 100 mm in width and about 30 mm to about 50 mm in length on the permeable topsheet. Even more preferably, the hydrophobic composition forms a substantially rectangular area of about 75 mm in width and about 40 mm in length. Still more preferably, the hydrophobic composition forms a substantially rectangular area of about 100 mm in width and about 75 mm in length on the permeable topsheet. Yet more preferably, the hydrophobic composition forms a substantially rectangular area of about 100 mm to about 120 mm in width and about 65 mm to about 85 mm in length on the permeable topsheet. Most preferably, the hydrophobic composition forms a substantially rectangular area of about 100 mm to about 140 mm in width and about 50 mm to about 100 mm in length on the permeable topsheet.

The leak protection zones on the flat tissue 60 are defined by a front edge and a back edge, said front and back edge being parallel to the front and back edge of the flat tissue 60, and first and second opposing edges, said first and second opposing edges being parallel to the opposing longitudinal side edges of the flat tissue 60. The front edge of the leak protection zone is preferably less than about 300 mm, more preferably less than about 220 mm and even more preferably less than about 100 mm from the front edge of the flat tissue 60. The back edge of the leak protection zone is preferably less than about 300 mm, more preferably less than about 220 mm and even more preferably less than about 100 mm from the back edge of the flat tissue 60.

The width of the leak protection zone or each leak protection zone of a plurality of leak protection zones is preferably about 30 mm to about 60 mm on the flat tissue 60.

A pair of leak protection zones are optionally located on the flat tissue 60. Preferably, the pair of leak protection zones are equidistant from a mid-line dissecting the flat tissue in the longitudinal direction into two equal halves. More preferably, the pair of leak protection zones are about 50 mm to about 150 mm apart. Even more preferably, the pair of leak protection zones correspond to about the longitudinal side edges of the absorbent core when the flat tissue is wrapped about said core.

The hydrophobic composition may partially or totally cover each leak protection zone. Whether the hydrophobic composition covers the entire leak protection zone or partially covers the leak protection zone may be determined by an optimization of cost-efficiency and effectiveness.

When the hydrophobic composition partially covers each leak protection zone, the hydrophobic composition may form a pattern on the leak protection zone. The patterns may be of any shape, size or variety. Preferably, the pattern is selected to increase cost-efficiency, increase effectiveness or optimize between cost-efficiency and effectiveness. Non-limiting exemplary patterns that may be formed by the hydrophobic composition at a leak protection zone include sets of vertical or horizontal lines, triangular shapes, square shapes, and/or circular shapes. In absorbent articles having a plurality of leak protection zones, the pattern may be the same or different from one zone to the next. Preferably, the pattern is selected to optimize cost-efficiency and effectiveness based on the physical characteristics determined at each particular site of the absorbent article where the leak protection zone is located.

The hydrophobic composition may be of any density effective in attaining leak protection. The hydrophobic composition may be a substantially uniform density or a non-uniform density. Moreover, the density of the hydrophobic composition may vary from one leak protection zone in an absorbent core to another. Preferably, the density of the hydrophobic composition is selected to optimize between cost-efficiency and effectiveness of the absorbent article, and/or method for preparing or using same. Preferably, the density of said hydrophobic composition is about 0.25 gsm to about 12 gsm; more preferably about 1 gsm to about 8 gsm; and even more preferably about 4 gsm to about 6 gsm.

Due to the wide variety of materials which may be incorporated into the absorbent articles of the present invention, the present invention is not intended to be limited to any specific materials. The topsheet, backsheet, absorbent core and other components of the absorbent articles in accordance with various implementations of the present invention may comprise various materials. Persons of ordinary skill in the art would be readily able to select appropriate materials for use in the various components of the present invention based upon the materials.

In accordance with various implementations of the present invention, the absorbent core may contain one or more fibers, one or more polymers or combinations thereof. Non-limiting exemplary fibers which may be used in the articles of the present invention include, without limitation, cellulose fibers, cellulose acetate fibers, rayon fibers, Courtauld's LYOCEL fibers, polyacrylonitrile fibers, surface modified (hydrophilic) polyester fibers, surface modified polyolophin/polyester bicomponent fibers, surface modified polyester/polyester bicomponent fibers, cotton fibers or blends thereof. Preferably cellulose acetate, rayon, Courtauld's LYOCEL, polyacrylonitrile, cotton fibers and cotton linters or combinations thereof are used in the process of the present invention. More preferably, cellulose fibers are used as the fiber material in the present invention.

Other materials may be added to the fiber or pulp material which is optionally processed in a fiberizing apparatus, such as a hammermill. The additives may be added at any point in the process. Preferably, the additives are sprayed or injected into the airborne fibers prior to the depositing of the fibers on the forming surface 2. Non-limiting exemplary additives which may be incorporated into the process of the present invention include a polymer such as a super absorbent polymer (SAP), hydrophilic polymers, potato starch, corn starch, wheat starch or rice starch, or combinations thereof. Various different combinations of materials may be used as are known to persons of ordinary skill in the art and which are described in U.S. Pat. No. 6,068,620 which is herein incorporated by reference. Preferably, the mixtures incorporated in the invention are substantially homogenous mixtures or uniformly distributed mixtures. Absorbent articles in accordance with an implementation of the present invention are prepared using conventional methods and materials well known to persons of ordinary skill in the art, using the guidelines provided herein. In one implementation of the present invention an absorbent article is prepared by a process comprising identifying one or more leak protection zones on an absorbent article; applying a hydrophobic composition to a permeable topsheet at the one or more leak protection zones on said permeable topsheet; and forming an absorbent article comprising said permeable topsheet, a substantially impermeable backsheet and an absorbent core disposed between said permeable topsheet and said substantially impermeable backsheet.

An implementation of the present invention provides a method for preparing an absorbent article comprising: identifying a leak protection zone or a plurality of leak protection zones; disposing a hydrophobic composition at one or more predetermined areas on a substrate; and forming an absorbent article comprising the substrate such that the one or more predetermined areas correspond to the leak protection zone or plurality of leak protection zones. Optionally, the hydrophobic composition is comprised of a substance effective for skin protection, a substance effective for skin care, a substance effective for skin wellness, a substance effective for skin improvement, a substance perceived as having a skin wellness benefit or combinations thereof.

Another implementation of the present invention provides a method for preparing an absorbent article comprising: disposing a hydrophobic composition at predetermined areas on a tissue layer or a permeable topsheet; and forming said tissue layer or permeable topsheet into an absorbent core such that the predetermined areas correspond to a leak protection zone or a plurality of leak protection zones. The hydrophobic composition is optionally comprised of a substance effective for skin protection, a substance effective for skin care, a substance effective for skin wellness, a substance effective for skin improvement, a substance perceived as having a skin wellness benefit or combinations thereof.

In a further implementation of the present invention, a method of preparing improved absorbent articles comprises wrapping the absorbent core in a tissue layer, said tissue layer comprising a hydrophobic composition at a leak protection zone or multiple leak protection zones. The hydrophobic composition is applied to the tissue layer at the leak protection zone using conventional techniques and methods readily available to persons of ordinary skill in the art. Non-limiting exemplary methods of applying the hydrophobic composition include spraying, coating, painting, pressing, layering, disbursing and/or combinations thereof. A person of ordinary skill in the art would readily be able to practice the methods of the present invention using said conventional methods and techniques, including selecting the most appropriate methods and techniques, based upon the guidance provided in the disclosure herein, without undue experimentation.

The hydrophobic composition may comprise a variety of substances. Preferably, the substance is selected from the group consisting of theobroma oil, cacao butter, cocoa butter, petrolatum, mineral jelly, white mineral oil, dimethicone, zinc oxide preparation, beeswax, lanolin, jojoba oil, chinese white, zinc white and combinations thereof.

The compositions of the present invention unexpectedly provide an absorbent article that displays superior leak protection and/or improved skin wellness. In one implementation of the present invention, a composition comprises: an effective amount of a hydrophobic substance selected from the group consisting of cocoa butter, petrolatum, dimethicone, zinc oxide and combinations thereof; wherein said hydrophobic substance is effective in providing leak protection during use when adhered to a leak protection zone on said absorbent article. Preferably, the hydrophobic substance is cocoa butter.

The present invention has been described in connection with the preferred embodiments. These embodiments, however, are merely for example and the invention is not restricted thereto. Any examples described herein are illustrative of preferred embodiments of the inventive subject matter and are not to be construed as limiting the inventive subject matter thereto. It will be understood by those skilled in the art that other variations and modifications can easily be made within the scope of the invention as defined by the appended claims.

What is claimed is:

1. An absorbent article comprising:
   a permeable topsheet;
   a substantially impermeable backsheet;
   an absorbent core positioned between said permeable topsheet and said substantially impermeable backsheet; and
   a hydrophobic composition disposed between the skin-opposing surface of the substantially impermeable backsheet and the skin of a wearer of the absorbent article at a first leak protection zone and a second leak protection zone, said first leak protection zone being located on the topsheet adjacent to and inward of the front edge of the absorbent article and positioned centrally between the two inner leg gathers, and said second leak protection zone being located near the back edge of the absorbent article and positioned centrally between the two inner leg gathers.

2. The absorbent article of claim 1, wherein the hydrophobic composition comprises a substance effective for skin protection, skin care, skin wellness, skin improvement, or a substance perceived as effective for skin wellness or combinations thereof.

3. The absorbent article of claim 1, wherein the hydrophobic composition comprises a hydrophobic substance selected from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof.

4. The absorbent article of claim 1, wherein the hydrophobic composition comprises cocoa butter.

5. The absorbent article of claim 1, wherein the hydrophobic composition comprises dimethicone.

6. The absorbent article of claim 1, wherein the hydrophobic composition comprises zinc oxide preparation.

7. The absorbent article of claim 1, wherein each leak protection zone is defined by a plurality of contact points on said permeable topsheet.

8. The absorbent article of claim 1, wherein each leak protection zone is defined by outside and inside opposing edges substantially parallel to the front and back perimeter of the permeable topsheet and located at a predetermined distance from said front and back perimeter.

9. The absorbent article of claim 1, wherein each leak protection zone is defined by outside and inside opposing edges substantially parallel to the front and back perimeter of the permeable topsheet, said outside opposing edge of each leak protection zone being about 0.25 mm to about 20 mm from the nearest said perimeter of the permeable topsheet.

10. The absorbent article of claim 1, wherein each leak protection zone is defined by outside and inside opposing edges substantially parallel to the front and back perimeter of the permeable topsheet, said outside opposing edge of each leak protection zone being about 2 mm to about 10 mm from the nearest said perimeter of the permeable topsheet.

11. The absorbent article of claim 1, wherein each leak protection zone is defined on an outside opposing edge by a first line substantially parallel to the front or back perimeter of the permeable topsheet and on an inside opposing edge by a second line substantially parallel to said outside opposing edge of the leak protection zone, said first line being about 100 mm from said second line.

12. The absorbent article of claim 1, wherein the hydrophobic composition totally covers the leak protection zone.

13. The absorbent article of claim 1, wherein the hydrophobic composition partially covers the leak protection zone.

14. The absorbent article of claim 1, wherein the hydrophobic composition is in contact with a portion of said permeable topsheet corresponding to the waist area of a wearer of said absorbent article.

15. The absorbent article of claim 1, wherein the hydrophobic composition forms a substantially rectangular area of about 100 mm to about 140 mmn in width and about 50 mm to about 100 mm in length.

16. The absorbent article of claim 1, wherein the hydrophobic composition forms a substantially rectangular area of about 100 mm to about 120 mm in width and about 65 mm to about 85 mm in length.

17. The absorbent article of claim 1, wherein the hydrophobic composition forms a substantially rectangular area of about 100 mm in width and about 75 mm in length.

18. The absorbent article of claim 1, wherein the hydrophobic composition forms a substantially rectangular area of about 30 mm to about 50 mm in length and about 50 mm to about 100 mm in width.

19. The absorbent article of claim 1, wherein the hydrophobic composition forms a substantially rectangular area of about 100 mm to about 120 mm in width and about 35 mm to about 45 mm in length.

20. The absorbent article of claim 1, wherein the hydrophobic composition forms a substantially rectangular area of about 40 mm in length and about 75 mm in width.

21. The absorbent article of claim 1, wherein the hydrophobic composition is in contact with a portion of the permeable topsheet.

22. The absorbent article of claim 1, wherein the hydrophobic composition is in contact with a portion of a tissue layer disposed between the absorbent core and the permeable topsheet.

23. The absorbent article of claim 1, wherein the hydrophobic composition partially covers a leak protection zone on the permeable topsheet.

24. The absorbent article of claim 23, wherein the hydrophobic composition forms a pattern on the leak protection zone.

25. The absorbent article of claim 1, wherein the hydrophobic composition is of a substantially uniform density.

26. The absorbent article of claim 1, wherein the hydrophobic composition is of a variable density.

27. The absorbent article of claim 1, wherein the density of said hydrophobic composition is about 0.25 gsm to about 12 gsm.

28. The absorbent article of claim 1, wherein the density of said hydrophobic composition is about 1 gsm to about 8 gsm.

29. The absorbent article of claim 1, wherein the density of said hydrophobic composition is about 4 gsm to about 6 gsm.

30. An absorbent article comprising:
a permeable topsheet
a substantially impermeable backsheet;
an absorbent core positioned between said permeable topsheet and said substantially impermeable backsheet; and
a hydrophobic composition disposed between the skin-opposing surface of the substantially impermeable backsheet and the skin of a wearer of the absorbent article at a first leak protection zone and a second leak protection zone, said first leak protection zone being located on the topsheet adjacent to and inward of the front edge of the absorbent article and positioned centrally between the two inner leg gathers, and said second leak protection zone being located near the back edge of the absorbent article and positioned centrally between the two inner leg gathers;
wherein said hydrophobic composition comprises a substance effective for skin protection, a substance effective for skin care, a substance effective for skin wellness, a substance effective for skin improvement, a substance perceived as having skin wellness benefits or combinations thereof.

31. The absorbent article of claim 30, wherein the hydrophobic substance is selected from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof.

32. The absorbent article of claim 30, wherein the hydrophobic composition comprises cocoa butter.

33. The absorbent article of claim 30, wherein the hydrophobic composition comprises dimethicone.

34. An absorbent article comprising:
a permeable topsheet;
a substantially impermeable backsheet;
an absorbent core disposed between the permeable topsheet and the substantial impermeable backsheet; and
a tissue layer disposed between the absorbent core and the permeable topsheet; and
a hydrophobic composition disposed on said tissue layer at a pair of leak protection zones extending longitudinally along the two opposing side edges of the tissue layer.

35. The absorbent article of claim 34, wherein the hydrophobic composition comprises a substance effective for skin protection, a substance effective for skin care, a substance effective for skin wellness, a substance effective for skin improvement, a substance perceived as having a skin wellness benefit or combinations thereof.

36. The absorbent article of claim 34, wherein the hydrophobic composition comprises a hydrophobic substance selected from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof.

37. The absorbent article of claim 34, wherein the hydrophobic composition comprises cocoa butter.

38. The absorbent article of claim 34, wherein the hydrophobic composition comprises dimethicone.

39. The absorbent article of claim 34, wherein the hydrophobic composition comprises a zinc oxide preparation.

40. The absorbent article of claim 34, wherein the leak protection zone is defined by a plurality of contact points on said tissue layer.

41. The absorbent article of claim 34, wherein each leak protection zone is defined by a front edge and a back edge, said front edge and said back edge being parallel to the front and back edge of the tissue layer.

42. The absorbent article of claim 34, wherein each leak protection zone is defined by a front edge and a back edge, said front edge and said back edge being parallel to the front and back edge of the tissue layer;
wherein the front edge of the leak protection zone is less than about 300 mm from the front edge of the tissue layer and the back edge of the leak protection zone is less than about 300 mm from the back edge of the leak protection zone.

43. The absorbent article of claim 34, wherein each leak protection zone is defined by a front edge and a back edge, said front edge and said back edge being parallel to the front and back edge of the tissue layer;
wherein the front edge of the leak protection zone is less than about 220 mm from the front edge of the tissue layer and the back edge of the leak protection zone is less than about 220 mm from the back edge of the leak protection zone.

44. The absorbent article of claim 34, wherein each leak protection zone is defined by a front edge and a back edge, said front edge and said back edge being parallel to the front and back edge of the tissue layer;
wherein the front edge of the leak protection zone is less than about 100 mm from the front edge of the tissue layer and the back edge of the leak protection zone is less than about 100 mmn from the back edge of the leak protection zone.

45. The absorbent article of claim 34, wherein the hydrophobic composition totally covers the leak protection zone.

46. The absorbent article of claim 34, wherein the hydrophobic composition partially covers the leak protection zone.

47. The absorbent article of claim 34, wherein the hydrophobic composition is disposed at a pair of leak protection zones on the tissue layer located equidistant from a mid-line dissecting the tissue layer in the longitudinal direction into two equal halfs;
wherein the pair of leak protection zones are about 50 mm to about 150 mm apart.

48. The absorbent article of claim 34, wherein the hydrophobic composition is in contact with a portion of said absorbent article corresponding to about the sides of the absorbent core.

49. The absorbent article of claim 34, wherein the hydrophobic composition forms a substantially rectangular area of about 30 mm to about 60 mm in width.

50. The absorbent article of claim 34, wherein the hydrophobic composition is in contact with a portion of the permeable topsheet.

51. The absorbent article of claim 34, wherein the hydrophobic composition is in contact with a portion of a tissue layer disposed between the absorbent core and the permeable topsheet.

52. The absorbent article of claim 34, wherein the hydrophobic composition partially covers a leak protection zone on the permeable topsheet.

53. The absorbent article of claim 52, wherein the hydrophobic composition forms a pattern on the leak protection zone.

54. The absorbent article of claim 34, wherein the hydrophobic composition is of a substantially uniform density.

55. The absorbent article of claim 34, wherein the density of said hydrophobic composition is about 0.25 mm to about 12 gsm.

56. The absorbent article of claim 34, wherein the density of said hydrophobic composition is about 1 gsm to about 8 gsm.

57. The absorbent article of claim 34, wherein the density of said hydrophobic composition is about 4 gsm to about 6 gsm.

58. An absorbent garment comprising:
a front and a rear waist portion cooperating to form a waist opening;
a crotch region formed between said front waist portion and said rear waist portion;
a pair of leg openings on opposed sides of the crotch region;
a permeable topsheet, a substantially impermeable backsheet and an absorbent core positioned between said topsheet and said backsheet;
a hydrophobic composition disposed between the skin-opposing surface of the substantially impermeable backsheet and the skin of a wearer of the absorbent article at a first leak protection zone and a second leak protection zone, said first leak protection zone being located on the topsheet adjacent to and inward of the front edge of the absorbent article and positioned centrally between the two inner leg gathers, and said second leak protection zone being located near the back edge of the absorbent article and positioned centrally between the two inner leg gathers.

59. The absorbent garment of claim 58, further comprising a first leg gather and a second leg gather.

60. The absorbent garment of claim 58, wherein the leak protection zone is located on the absorbent article facing surface of the permeable topsheet in an area between the first leg gather and the second leg gather.

61. The absorbent garment of claim 58, further comprising a tissue layer disposed adjacent the skin-opposing surface of said permeable topsheet.

62. The absorbent garment of claim 61, wherein said tissue layer comprises a hydrophobic composition disposed at a leak protection zone.

63. A method for preparing an absorbent article comprising:
disposing a hydrophobic composition on a topsheet adjacent to and inward of a front edge or back edge and positioned centrally and/or on a tissue layer longitudinally along the two opposing side edges of said tissue layer; and
forming an absorbent article comprising the topsheet and/or tissue layer.

64. The method of claim 63, further comprising disposing the absorbent core in a tissue layer, said tissue layer comprising a hydrophobic composition at a leak protection zone or a plurality of leak protection zones.

65. A method for preparing an absorbent article comprising:
- disposing a hydrophobic composition at predetermined areas on a tissue layer or permeable topsheet;
- forming said tissue layer or permeable topsheet into an absorbent core such that the predetermined areas correspond to a pair of leak protection zones extending longitudinally along the two opposing side edges of the tissue layer or to a pair of leak protection zones located on a topsheet adjacent to and inward of the front edge and/or back edge and positioned centrally.

66. The method of claim 65, wherein the hydrophobic composition comprises a substance effective for skin protection, a substance effective for skin care, a substance effective for skin wellness, a substance effective for skin improvement or combinations thereof.

67. The method of claim 65, wherein the hydrophobic composition is selected from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof.

68. The method of claim 65, wherein the hydrophobic composition is cocoa butter.

69. The method of claim 65, wherein the hydrophobic composition is a zinc oxide preparation.

70. A composition in an absorbent article for providing leak protection and improved skin wellness comprising:
- a hydrophobic substance selected from the group consisting of cocoa butter, petrolatum, dimethicone, a zinc oxide preparation, beeswax, lanolin, jojoba oil and combinations thereof;
- wherein said hydrophobic substance is effective in providing leak protection during use of the absorbent article when disposed at a pair of leak protection zones extending longitudinally along two opposing side edges of a tissue layer or at a pair of leak protection zones being located on a topsheet adjacent to and inward of a front edge and/or a back edge of the absorbent article and positioned centrally between two inner leg gathers.

71. The composition of claim 70, wherein the hydrophobic substance is disposed on a permeable topsheet of the absorbent article.

72. The composition of claim 70, wherein the hydrophobic substance is disposed on a tissue layer of an absorbent article.

73. The composition of claim 70, wherein the hydrophobic substance is cocoa butter.

74. The composition of claim 70, wherein the hydrophobic substance is a zinc oxide preparation.

* * * * *